(12) United States Patent
Dewey

(10) Patent No.: US 11,166,825 B1
(45) Date of Patent: Nov. 9, 2021

(54) SPINAL IMPLANT

(71) Applicant: WARSAW ORTHOPEDIC, INC., Warsaw, IN (US)

(72) Inventor: Jonathan M. Dewey, Memphis, TN (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 0 days.

(21) Appl. No.: 16/917,969

(22) Filed: Jul. 1, 2020

(51) Int. Cl.
*A61F 2/44* (2006.01)
*A61F 2/46* (2006.01)

(52) U.S. Cl.
CPC .......... *A61F 2/4455* (2013.01); *A61F 2/442* (2013.01); *A61F 2/4611* (2013.01)

(58) Field of Classification Search
CPC .......................... A61F 2/44; A61F 2/4455–447
See application file for complete search history.

(56) References Cited

U.S. PATENT DOCUMENTS

| | | | |
|---|---|---|---|
| 6,723,097 B2 | 4/2004 | Fraser et al. |
| 7,156,875 B2 | 1/2007 | Michelson |
| 7,763,078 B2 | 7/2010 | Peterman et al. |
| 7,776,049 B1 | 8/2010 | Curran |
| 7,905,886 B1 | 3/2011 | Curran |
| 8,062,375 B2 | 11/2011 | Glerum et al. |
| 8,092,464 B2 | 1/2012 | McKay |
| 8,308,805 B2 | 11/2012 | Lynn |
| 8,556,979 B2 | 10/2013 | Glerum et al. |
| 8,672,948 B2 | 3/2014 | Lemaitre |
| 9,028,553 B2 | 5/2015 | Lindenmann |
| 9,084,688 B2 | 7/2015 | Hes |
| 9,216,098 B2 | 12/2015 | Trudeau et al. |
| 9,381,098 B2 | 7/2016 | Gittings et al. |
| 9,693,882 B2 | 7/2017 | Lomeli et al. |
| 9,730,802 B1 | 8/2017 | Harvey |
| 9,737,415 B2 | 8/2017 | Foley |
| 9,895,236 B2 | 2/2018 | Voellmicke |
| 10,238,503 B2 | 3/2019 | Branch et al. |
| 10,251,759 B2 | 4/2019 | Butler |
| 10,575,962 B2 | 3/2020 | Dewey et al. |
| 10,736,756 B2 | 8/2020 | Dewey et al. |
| 2004/0162616 A1 | 8/2004 | Simonton |
| 2004/0186572 A1 | 9/2004 | Lange |
| 2005/0154459 A1* | 7/2005 | Wolek ........................ A61F 2/44 623/17.11 |
| 2005/0159815 A1* | 7/2005 | Kamimura ............. A61B 17/70 623/17.11 |

(Continued)

FOREIGN PATENT DOCUMENTS

WO  WO 2001/095838  12/2001
WO  WO 2004/019829   3/2004

(Continued)

*Primary Examiner* — Eduardo C Robert
*Assistant Examiner* — Michelle C Eckman

(57) ABSTRACT

An interbody spinal implant for implantation in a disc space between adjacent vertebral bodies, and an insertion instrument facilitating such implantation is provided. The spinal implant includes a body portion and an extended end portion, where at least the body portion can include a biconvex upper and lower surfaces. And the insertion instrument is engageable to a proximal end portion of the interbody spinal implant to facilitate insertion of the interbody spinal implant into the disc space.

20 Claims, 7 Drawing Sheets

(56) References Cited

U.S. PATENT DOCUMENTS

| | | |
|---|---|---|
| 2006/0167461 A1 | 7/2006 | Hawkins et al. |
| 2006/0217806 A1 | 9/2006 | Peterman |
| 2006/0217807 A1 | 9/2006 | Peterman |
| 2006/0253201 A1 | 11/2006 | McLuen |
| 2007/0032872 A1 | 2/2007 | Simonton |
| 2007/0093898 A1 | 4/2007 | Schwab |
| 2008/0015695 A1 | 1/2008 | Eckman |
| 2008/0262623 A1 | 10/2008 | Bagga |
| 2010/0076559 A1 | 3/2010 | Bagga |
| 2010/0198263 A1 | 8/2010 | Siegal et al. |
| 2011/0092976 A1 | 4/2011 | Rawles et al. |
| 2011/0106261 A1 | 5/2011 | Chin |
| 2011/0172774 A1 | 7/2011 | Varela |
| 2011/0208309 A1 | 8/2011 | Peterson et al. |
| 2012/0059470 A1 | 3/2012 | Weiman |
| 2012/0158147 A1 | 6/2012 | Glerum |
| 2012/0165945 A1 | 6/2012 | Hansell |
| 2012/0232664 A1 | 9/2012 | Ulrich, Jr. |
| 2012/0239150 A1 | 9/2012 | Ullrich, Jr. |
| 2012/0239151 A1 | 9/2012 | Ulrich, Jr. |
| 2013/0158664 A1 | 6/2013 | Palmatier |
| 2013/0158669 A1 | 6/2013 | Sungarian et al. |
| 2014/0100662 A1 | 4/2014 | Patterson et al. |
| 2014/0114421 A1 | 4/2014 | Ullrich, Jr. |
| 2014/0228955 A1 | 8/2014 | Weiman |
| 2014/0249630 A1 | 9/2014 | Weiman |
| 2014/0277485 A1 | 9/2014 | Johnson |
| 2014/0330383 A1 | 11/2014 | Wimberley |
| 2014/0343678 A1 | 11/2014 | Suddaby et al. |
| 2015/0025636 A1 | 1/2015 | Lim et al. |
| 2015/0100128 A1 | 4/2015 | Glerum et al. |
| 2015/0100129 A1 | 4/2015 | Waugh |
| 2015/0112442 A1 | 4/2015 | Foley |
| 2015/0173917 A1 | 6/2015 | Radcliffe et al. |
| 2015/0216670 A1 | 8/2015 | Davenport et al. |
| 2015/0250610 A1 | 9/2015 | Jacobs |
| 2015/0272743 A1 | 10/2015 | Jimenez et al. |
| 2015/0272746 A1 | 10/2015 | Jimenez et al. |
| 2015/0342757 A1 | 12/2015 | Lomeli et al. |
| 2015/0374508 A1 | 12/2015 | Sandul |
| 2016/0058571 A1 | 3/2016 | McLaughlin |
| 2016/0113775 A1 | 4/2016 | Willis |
| 2016/0120660 A1 | 5/2016 | Melkent et al. |
| 2016/0213488 A1* | 7/2016 | Moore .................. A61F 2/4465 |
| 2016/0262909 A1 | 9/2016 | Lindenmann et al. |
| 2016/0270931 A1 | 9/2016 | Trieu |
| 2016/0310294 A1* | 10/2016 | McConnell ........... A61F 2/4684 |
| 2016/0374826 A1 | 12/2016 | Palmatier et al. |
| 2017/0095335 A1 | 4/2017 | Kieser |
| 2017/0105844 A1 | 4/2017 | Kuyler et al. |
| 2017/0112630 A1 | 4/2017 | Kuyler |
| 2017/0189200 A1 | 7/2017 | Miller et al. |
| 2017/0239067 A1 | 8/2017 | Nino |
| 2018/0116815 A1 | 5/2018 | Branch et al. |
| 2018/0235778 A1 | 8/2018 | Nino |
| 2019/0076266 A1 | 3/2019 | Trudeau |
| 2019/0151111 A1 | 5/2019 | Dewey et al. |
| 2019/0247197 A1 | 8/2019 | Jagannathan |
| 2019/0247203 A1 | 8/2019 | Nino |
| 2019/0298545 A1 | 10/2019 | Dewey et al. |
| 2019/0298546 A1 | 10/2019 | Dewey et al. |

FOREIGN PATENT DOCUMENTS

| | | |
|---|---|---|
| WO | WO 2008/155472 | 12/2008 |
| WO | WO 2010/148112 | 12/2010 |
| WO | WO 2015/085111 | 11/2015 |

* cited by examiner

SPINAL IMPLANT

FIELD

The present technology generally relates to an interbody spinal implant for implantation in a disc space between adjacent vertebral bodies, and an insertion instrument facilitating such insertion.

BACKGROUND

Conventional interbody spinal fusion implants have been used to facilitate spinal fusion between adjacent vertebral bodies across a disc space. One or more of the conventional interbody spinal implants have been inserted into the disc space such that an upper surface thereof contacts an upper one of the adjacent vertebral bodies and a lower surface thereof contacts a lower one of the adjacent vertebral bodies. The vertebral bodies are composed of cancellous bone surrounded by a layer of cortical bone. The cortical bone is harder than the cancellous bone, and the cortical bone is thickest around the perimeters of the endplates. Thus, the bone of endplates of the adjacent vertebral bodies is softer near the center of the endplates, and is harder around the perimeter of the endplates. Depending on the position of the conventional interbody spinal implants within the disc space, such conventional interbody spinal fusion implants can potentially subside into the endplates of the upper one and the lower one of the adjacent vertebral bodies. Therefore, there is a need for interbody spinal implants configured to engage substantial portions of the perimeters of the endplates of the adjacent vertebral bodies to limit such subsistence, and there is a need for an insertion instrument facilitating such implantation.

SUMMARY

The techniques of this disclosure generally relate to an interbody spinal implant for implantation in a disc space between adjacent vertebral bodies, and an insertion instrument facilitating such implantation.

In one aspect, the present disclosure provides an interbody spinal implant for implantation into a disc space between an upper vertebral body and a lower vertebral body, the implant including a body portion having a proximal first end, an opposite distal second end, a proximal end surface at and adjacent the proximal first end, an upper surface, a lower surface, a first lateral side surface, a second lateral side surface, and a first mid-longitudinal axis extending through the proximal first end and the distal second end of the body portion, the upper surface and the lower surface each being at least in part arcuate in a first plane perpendicular to the first mid-longitudinal axis, the upper surface and the lower surface each being at least in part arcuate in a second plane extending along the first mid-longitudinal axis and perpendicular to the first plane, and the proximal end surface being arcuate in a third plane extending along the first mid-longitudinal axis and perpendicular to the first plane; and an extended end portion having a proximal first end, an opposite distal second end, a distal end surface, an upper surface, a lower surface, a first lateral side surface, a second lateral side surface, and a second mid-longitudinal axis extending through the proximal first end and the distal second end of the extended end portion, the proximal first end of the extended end portion being collocated with the distal second end of the body portion, and the second mid-longitudinal axis being transverse to the first mid-longitudinal axis, where the upper surface and the lower surface being arcuate in the first plane and the second plane provides for biconvex configurations adapted to contact endplates of the upper vertebral body and the lower vertebral body, respectively.

In one aspect, the present disclosure provides interbody spinal implant including a body portion having a proximal first end, an opposite distal second end, a proximal end surface at and adjacent the proximal first end, an upper surface, a lower surface, a first lateral side surface, a second lateral side surface, and a first mid-longitudinal axis extending through the proximal first end and the distal second end of the body portion, the upper surface and the lower surface each being at least in part arcuate in a first plane perpendicular to the first mid-longitudinal axis, the upper surface and the lower surface each being at least in part arcuate in a second plane extending along the first mid-longitudinal axis and perpendicular to the first plane, and the proximal end surface being arcuate in a third plane extending along the first mid-longitudinal axis and perpendicular to the first plane; and an extended end portion having a proximal first end, an opposite distal second end, a distal end surface, an upper surface, a lower surface, a first lateral side surface, a second lateral side surface, and a second mid-longitudinal axis extending through the proximal first end and the distal second end of the extended end portion, the proximal first end of the extended end portion being collocated with the distal second end of the body portion, the second mid-longitudinal axis being transverse to the first mid-longitudinal axis, and portions of the extended end portion being located on each side of a fourth plane extending along the second lateral side surface.

In one aspect, the present disclosure provides an interbody spinal implant including a body portion having a proximal first end, an opposite distal second end, a proximal end surface at and adjacent the proximal first end, an upper surface, a lower surface, and a first mid-longitudinal axis extending through the proximal first end and the distal second end of the body portion, the upper surface and the lower surface each being at least in part arcuate in a first plane perpendicular to the first mid-longitudinal axis, and the proximal end surface being arcuate in a third plane extending along the first mid-longitudinal axis and perpendicular to the first plane; and an extended end portion having a proximal first end, an opposite distal second end, a distal end surface, an upper surface, a lower surface, and a second mid-longitudinal axis extending through the proximal first end and the distal second end of the extended end portion, the proximal first end of the extended end portion being collocated with the distal second end of the body portion, the second mid-longitudinal axis being transverse to the first mid-longitudinal axis, and portions of the extended end portion being located on each side of a fourth plane extending along the second lateral side surface.

The details of one or more aspects of the disclosure as set forth in the accompanying drawings and the description below. Other features, objects, and advantages of the techniques described in this disclosure will be apparent from the description and drawings, and from the claims.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

An interbody spinal implant according to one embodiment of the present disclosure is generally referenced by the numeral 10 in FIGS. 1-3 and 5. The spinal implant 10 is generally shaped like a hockey stick, and is configured for insertion into a disc space between adjacent vertebral bodies. The general hockey-stick shape of the spinal implant 10 is afforded by a body portion 12 and an extended end portion 14 that extends outwardly from the body portion 12.

Figure 1:
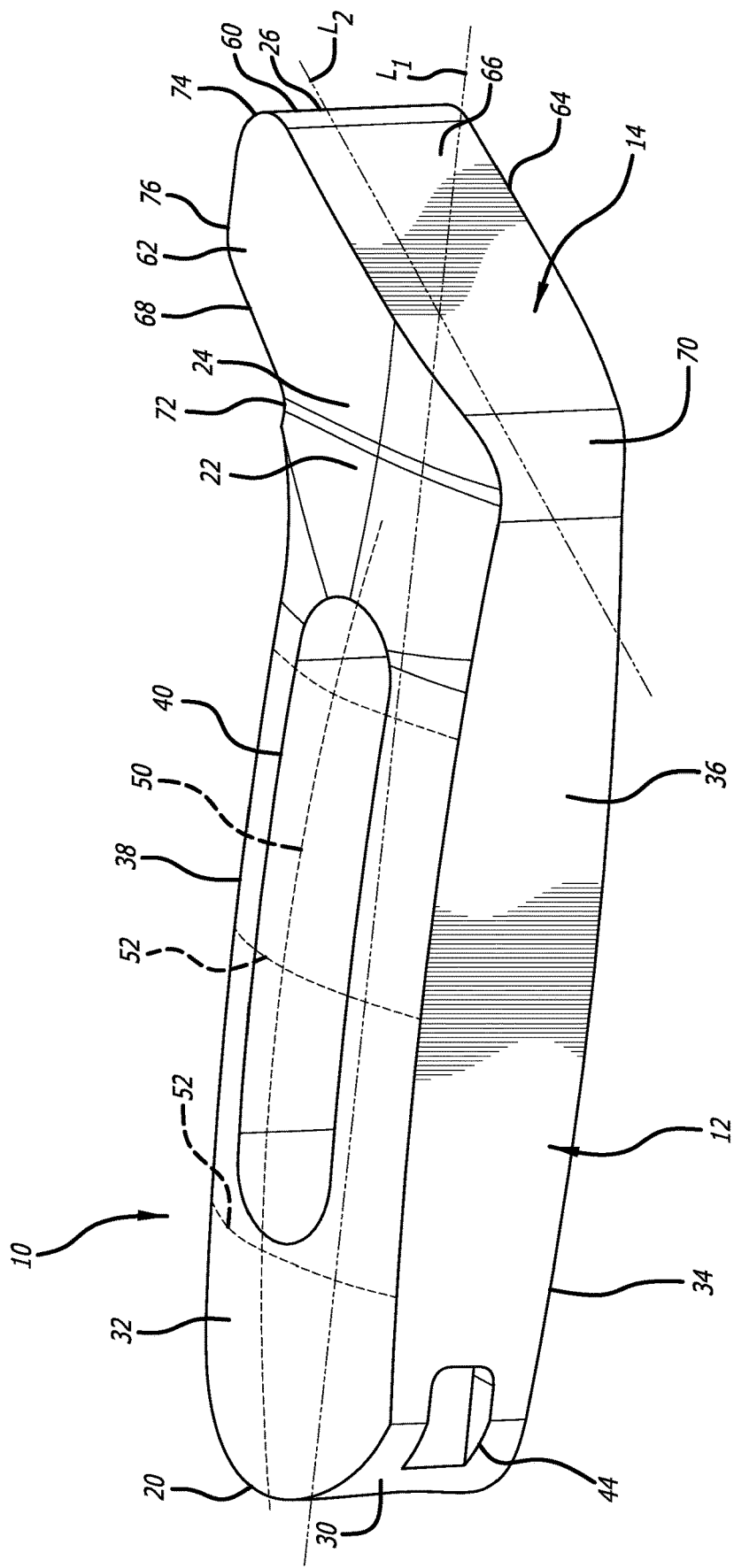
FIG. 1 is a side, top, perspective view that illustrates an interbody spinal implant according to a first embodiment of the present disclosure.
Figure 2:
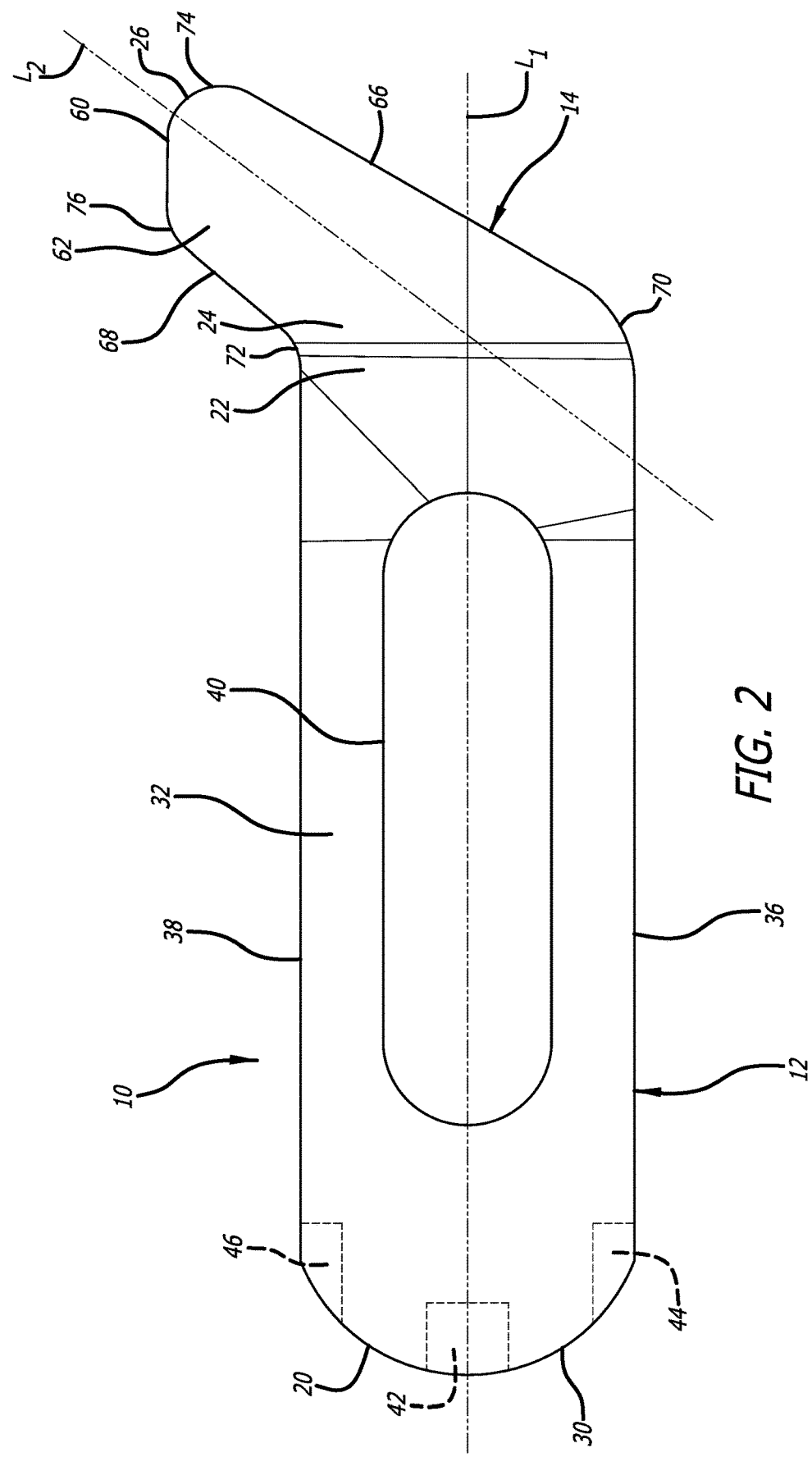
FIG. 2 is a top, plan view of the spinal implant of FIG. 1.

As depicted in FIGS. 1 and 2, the body portion 12 includes a proximal end 20, an opposite distal end 22, and a mid-longitudinal axis $L_1$ extending through the proximal end 20 and the distal end 22, and the extended end portion 14 includes a proximal end 24, an opposite distal end 26, and a mid-longitudinal axis $L_2$ extending through the proximal end 24 and the distal end 26. Furthermore, the distal end 22 of the body portion 12 and the proximal end 24 of the extended end portion 14 can be collocated with one another.

The body portion 12, as depicted in FIG. 1, includes a proximal end surface 30, an upper surface 32, a lower surface 34, a first lateral side surface 36, and a second lateral side surface 38. As discussed below, the upper surface 32 and/or the lower surface 34 can be bowed outwardly and have generally biconvex shapes to generally match the surrounding anatomy after implantation. Furthermore, the first lateral side surface 36 and/or the second lateral side surface 38 also can be bowed outwardly with convex shapes to generally match the surrounding anatomy after implantation. An optional elongated aperture 40 can extend through the body portion 12 between the upper surface 32 and the lower surface 34. The elongated aperture 40 can be used to facilitate bone growth through the spinal implant 10 between the adjacent vertebral bodies to facilitate spinal fusion. The body portion 12 (as well as the extended end portion 14) also can be made of a porous or semi-porous material to facilitate bone growth into the spinal implant 10 from the adjacent vertebral bodies to facilitate spinal fusion. Furthermore, the proximal end surface 30 can be the trailing end of the spinal implant 10, and the proximal end surface 30, the first side surface 36, and the second side surface 38 extend between the upper surface 32 and the lower surface 34.

The proximal end surface 30 (FIGS. 1 and 2) can be arcuate in first planes that are parallel to the mid-longitudinal axis $L_1$ and perpendicular to portions of the first side surface 36 and the second side surface 38. For example, the proximal end surface 30 is shaped as a portion of a circle in one of the first planes that extends along the mid-longitudinal axis $L_1$ and bisects the body portion 12 into an upper half and a lower half, and can be arcuate in other first planes that are parallel to the first plane bisecting the body portion 12. The arcuate shape of the proximal end surface 30 aids in preventing harm to anatomical structures adjacent to the spinal implant 10. Rather than being circular, the proximal end surface 30 can have other arcuate shapes. In some instances, the proximal end surface 30 can have arcuate bulges in the first planes adjacent the first side surface 36 and/or a second side surface 38.

The arcuate shape of the proximal end surface 30 aids in preventing harm to anatomical structures adjacent to the spinal implant. Furthermore, as depicted in FIGS. 1 and 2, the proximal end surface 30 can include a tool-engaging aperture 42 formed therein, the proximal end surface 30 and/or the first side surface 36 can include a first tool-engaging recess 44, and the proximal end surface 30 and/or the second side surface 38 can include a second tool-engaging recess 46. The tool-engaging aperture 42 can include threads (not shown) to facilitate engagement with a complimentary structure provided on an insertion tool 100. The first tool-engaging recess 44 can be formed in both the proximal end surface 30 and the first side surface 36, and the second tool-engaging recess 46 can be formed in both the proximal end surface 30 and the second side surface 38. Alternatively to the first tool-engaging recess 44 and the second tool-engaging recess 46, positive, negative, or a combination of positive/negative features can be formed on the proximal end surface 30, the first side surface 36, and the second side surface 38 to facilitate engagement with complimentary features formed on the insertion tool 100.

The upper surface 32 and the lower surface 34 can each have convex shapes. To illustrate, the upper surface 32 and/or the lower surface 34 can be convex in second planes that are aligned with the mid-longitudinal axis $L_1$ and perpendicular to the first plane bisecting the body portion 12, and/or can be convex in third planes transverse to the mid-longitudinal axis and perpendicular to both the first plane bisecting the body portion 12 and the second planes. The convexity of the upper surface 32 (which can be duplicated on the lower surface 34) is illustrated by a dashed line 50 and dashed lines 52 in FIG. 1, and such convexity can be described as being biconvex. The convexities of the upper surface 32 and the lower surface 34 facilitate engagement with portions of concave endplates of the adjacent vertebral bodies. The upper surface 32 and/or the lower surface 34 can be smooth or smoothened, or can include surface configurations such as a collection of surface roughenings to facilitate insertion of the spinal implant 10 into the disc space, and/or to facilitate bone ingrowth into the spinal implant 10. For example, while still being biconvex, the upper surface 32 and/or the lower surface 34 can include ratchetings that facilitate insertion of the spinal implant 10 into the disc space. Furthermore, while still being biconvex, the upper surface 32 and/or the lower surface 34 can be rough and porous to facilitate bone ingrowth into the spinal implant.

Additionally, the upper surface 32 and/or the lower surface 34 can be formed from a series or collection of surface configuration such as flats, convexities, concavities, and/or facets that together provide for a generally biconvex shape. To illustrate, a combination of convexities and concavities forming a generally biconvex shape could resemble the surface of a golf ball. Such a generally biconvex shape of the upper surface 32 and/or the lower surface 34 also can be formed by a series or collection of various surface configuration such as bumps, spikes, teeth, and/or ridges in addition or alternatively to the above-discussed ratchetings. Furthermore, such a generally biconvex shape of the upper surface 32 and/or the lower surface 34 also can be formed from a series or collection of terraced features arranged in a stair-step fashion. Alternatively, the upper surface 32 and/or the lower surface 34 can be formed as concave bowls for receiving bone graft that can be mounded into generally biconvex shapes.

The extended end portion 14, as depicted in FIG. 1, includes a distal end surface 60, an upper surface 62, a lower surface 64, a first side surface 66, and a second side surface 68. The distal end surface 60 and/or the first side surface 66, like the first lateral side surface 36 and/or the second lateral side surface 38, can be bowed outwardly with convex shapes to generally match the surrounding anatomy after implantation. The extended end portion 14 resides on both sides of a fourth plane that extends along the second side surface 38. Furthermore, the distal end surface 60, the first side surface 66, and the second side surface 68 extend between the upper surface 62 and the lower surface 64. The upper surface 62 and/or the lower surface 64 can be smooth or smoothened, or can include the above-discussed surface configurations. The upper surface 62 of the extended end portion 14 can smoothly transition into the upper surface 32 of the body portion 12, the lower surface 64 of the extended end portion 14 can smoothly transition into the lower surface 34 of the body portion 12, the first side surface 66 of the extended end portion 14 can smoothly transition into the first side surface 36 of the body portion 12, and the second side surface 68 of the extended end portion 14 can smoothly transition into the second side surface 38 of the body portion 12. For example, the smooth transition between first side surface 66 and the first side surface 36 is formed by a convex transition 70, and the smooth transition between the second side surface 68 and the second side surface 38 is formed by a concave transition 72.

In addition to the convex transition 70 and the concave transition 72, curved transitions can also be provided between the distal end surface 60, and the first side surface 66 and the second side surface 68. To illustrate, a first curved transition 74 can be provided between the distal end surface 60 and the first side surface 66, and a second curved transition 76 can be provided between the distal end surface 60 and the second side surface 68. Depending on the orientation of the spinal implant 10 during insertion, the distal surface 60, the first side surface 66, the first curved transition 74, or the second curved transition 76 can be the leading end surface.

The extended end portion 14 can be tapered such that the height thereof decreases from the proximal end 24 to the distal end 26, or can be reverse-tapered such that the height thereof increases from the proximal end 24 to the distal end 26. The tapering of the extended end portion 14 can be provided to accommodate the anatomy of the disc space and/or provided to facilitate insertion of the spinal implant 10 into the disc space. For example, as depicted in FIG. 1, the extended end portion 14 is reverse-tapered from the proximal end 24 to the distal end 26, and the heights of the first side surface 66 and the second side surface 68 can increase from the proximal end 24 to the distal end 26 of the extended end portion 14.

The upper surface 62 and/or the lower surface 64 can each be flattened or have convex shapes like the upper surface 32 and the lower surface 34. The upper surface 62 and/or the lower surface 64 can also have the above-discussed series or collection of surface configurations. To illustrate, in similar fashion to the upper surface 32 and the lower surface 34, the upper surface 62 and/or the lower surface 64 can be convex in planes aligned with and/or transverse to the mid-longitudinal axis $L_2$ of the extended end portion 14. The upper surface 62 (FIG. 1) and the lower surface 64 are substantially flattened except for the smooth transitions thereof into the upper surface 32 and the lower surface 34 of the body portion 12. Given that the extended end portion 14 has a reverse-taper from the proximal end 24 to the distal end 26, the upper surface 62 is angled upwardly from the proximal end 24, and the lower surface 64 is angled downwardly from the proximal end 24.

Figure 3:
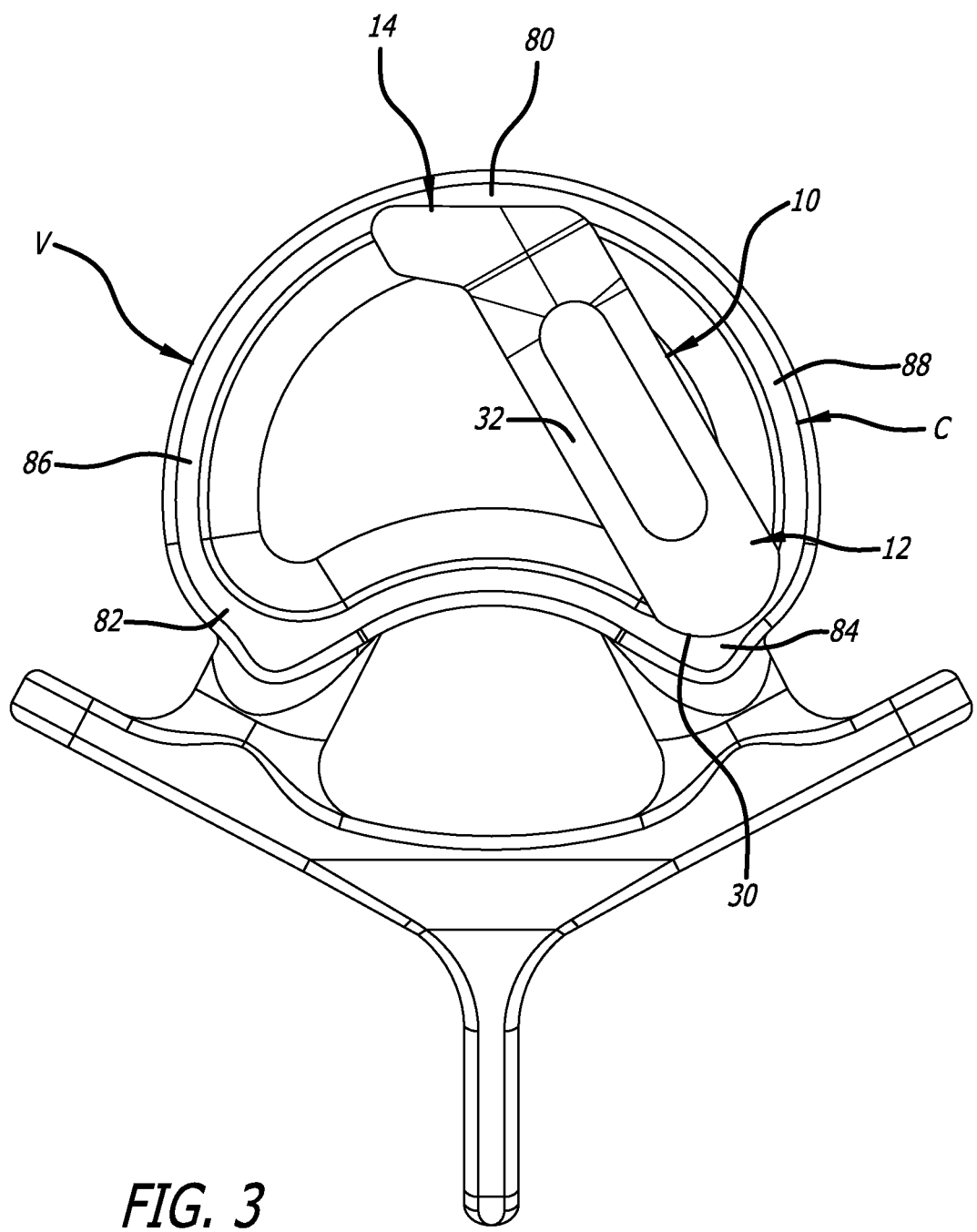
FIG. 3 is a top, plan view of the spinal implant of FIG. 1 in position on a lower one of adjacent vertebral bodies in a disc space.
Figure 5:
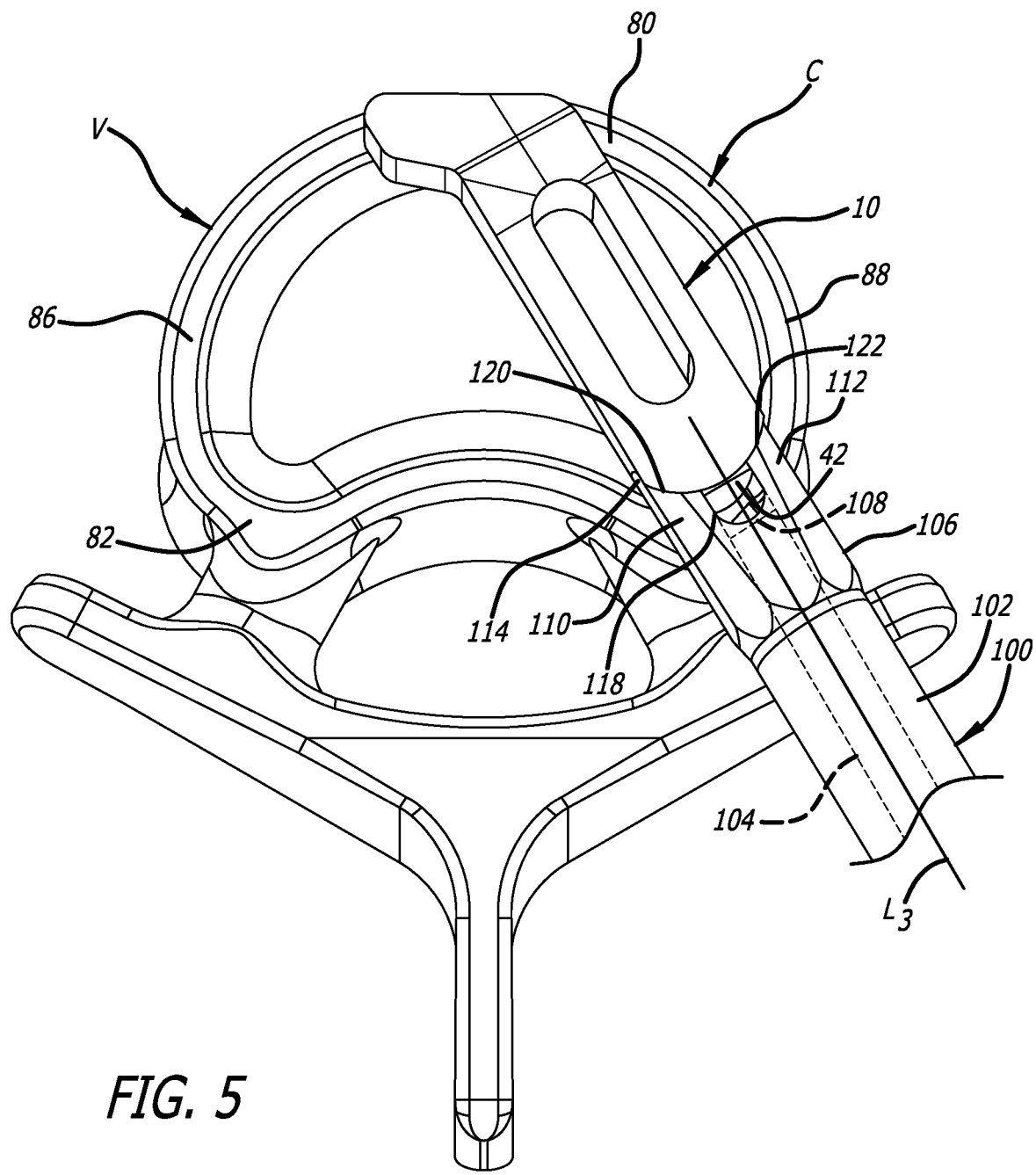
FIG. 5 is a top, rear, perspective view that illustrates insertion of the spinal implant of FIG. 1 into position relative to a lower one of adjacent vertebral bodies in a disc space using a first embodiment of an insertion instrument of the present disclosure.

When inserted into the disc space, the over-all shape of the spinal implant 10 affords placement of portions thereof on or adjacent the stronger bone of the cortical rims of the adjacent vertebra. As depicted in FIGS. 3 and 5, the spinal implant 10 is positioned such that a portion of the extended end portion 14 adjacent the first side surface 66 is positioned on a cortical rim C of a lower vertebral body V, and a portion of the body portion 12 adjacent the proximal end surface 30 is also positioned on the cortical rim C of the lower vertebral body V. The cortical rim C of the lower vertebral body V includes an anterior portion 80, a first posterior portion 82, a second posterior portion 84, a first lateral portion 86, and a second lateral portion 88. The portion of the extended end portion 14, as depicted in FIGS. 3 and 5, rests on a portion of the anterior portion 80 of the cortical rim C. Furthermore, as depicted in FIGS. 3 and 5, the portion of the body portion 12 rests on portions of the second posterior portion 84 and the second lateral portion 88 of the cortical rim C. The arcuate shape of the proximal end surface 30 and the smooth transitions of the proximal end surface 30 into the first lateral side surface 36 and a second lateral side surface 38 serve in preventing harm to the anatomical structures adjacent to the spinal implant 10 by distributing the load of the spinal implant 10 across the stronger bone of the cortical rim C over a larger area of the spinal implant 10, as well to generally approximate the curvature of the cortical rim C.

Although not shown, the spinal implant 10 would also contact similar locations of a cortical rim of an upper vertebral body across the disc space from the lower vertebral body V. Given the placement of the spinal implant 10, the arcuate shapes of the upper surface 62 and the lower surface 64 facilitate the distribution of the load to the strongest bone of the vertebral bodies at the cortical rim C.

The insertion tool 100 can be used to facilitate positioning the spinal implant 10 in the disc space. Furthermore, the spinal implant 10, as depicted in FIG. 5, can be inserted into the disc space from substantially lateral or substantially posterior directions as part of a transforminal lumber interbody fusion (TLIF) procedure or a posterior lumbar interbody fusion (PLIF) procedure, respectively. The spinal implant 10 could also be inserted from additional different insertion directions, and with different positions for the tool-engaging aperture 42, the first tool-engaging recess 44, the second tool-engaging recess 46, or other engagement features, the spinal implant 10 could be inserted in different orientations relative to the insertion tool 100. For example, the tool-engaging aperture 42, the first tool-engaging recess 44, the second tool-engaging recess 46, or other engagement features could be provided on the extended end portion 14, and the insertion tool 100 could be used to insert the spinal implant 10 at an insertion orientation afforded by the different placement of these engagement features.

Figure 4:
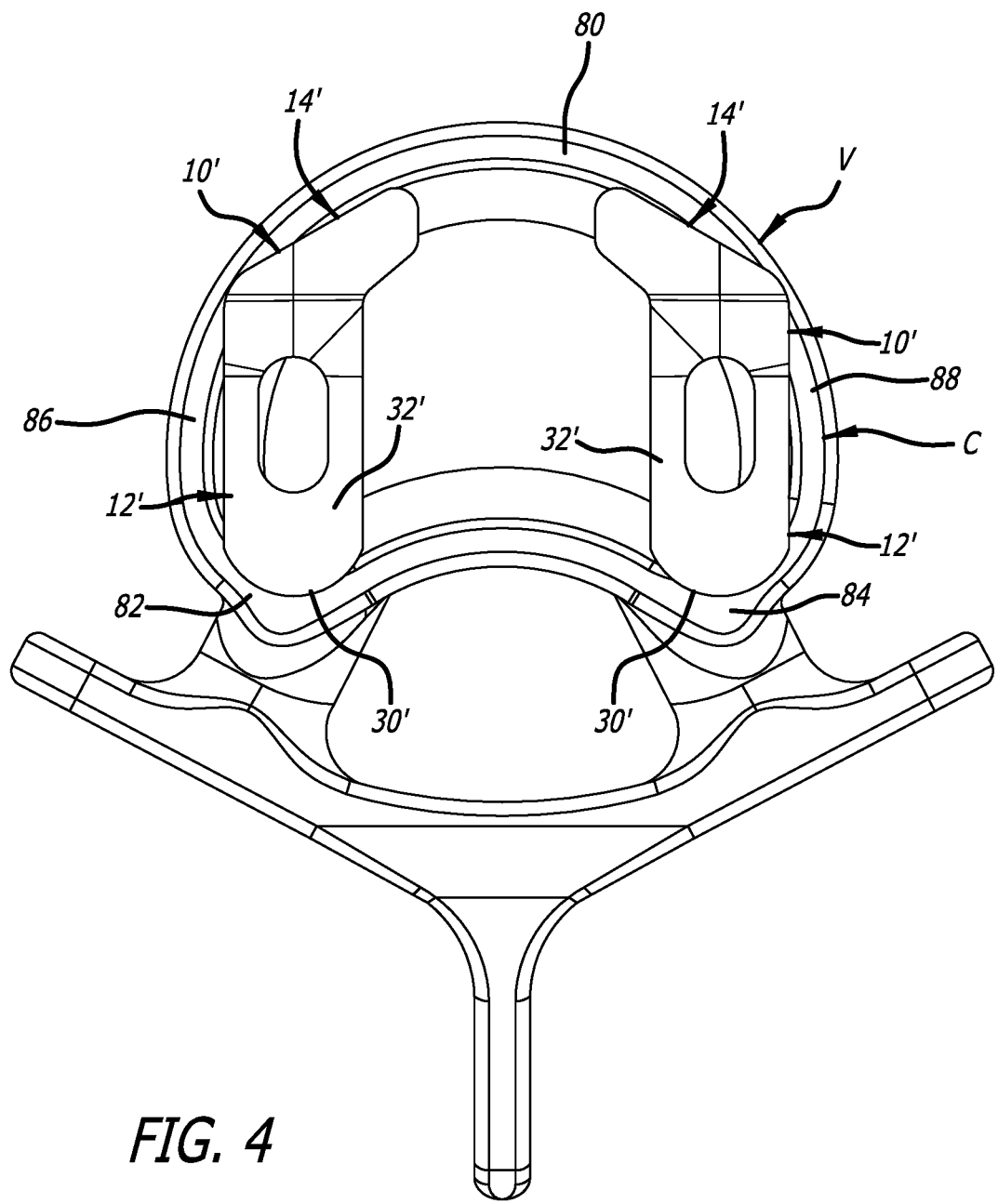
FIG. 4 is a top, plan view that illustrates interbody spinal implants according to a second embodiment of the present disclosure in positions on a lower one of adjacent vertebral bodies in a disc space.
Figure 6:
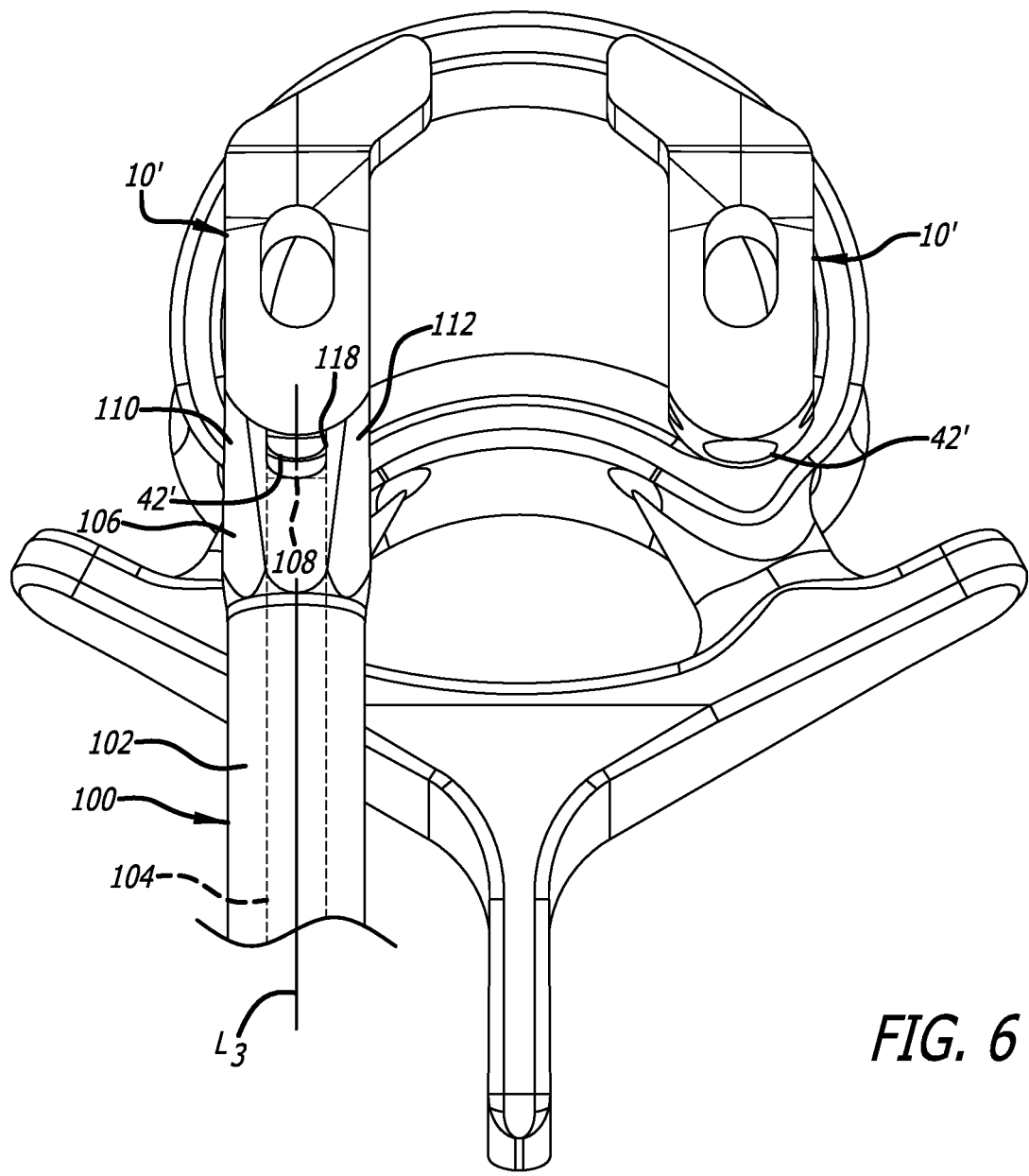
FIG. 6 is a top, rear, perspective view that illustrates insertion of the spinal implants of FIG. 4 into position relative to a lower one of adjacent vertebral bodies in a disc space using the insertion instrument of FIG. 5.

One or more smaller spinal implants 10' similar to the spinal implant 10 and having similar features thereto can be used instead of the spinal implant 10, and similar numerals will be used in describing the spinal implants 10'. As depicted in FIGS. 4 and 6, a body portion 12' has a similar width to the body portion 12 and includes a proximal end surface 30', but is shorter than the body portion 12, and an extended end portion 14' has similar dimensions as the extended end portion 14.

As depicted in FIGS. 4 and 6, when inserted into the disc space, the spinal implants 10' are sized such that two spinal implants 10' can be positioned such that a first of the spinal implants 10' is positioned on portions of the anterior portion 80, the first lateral portion 86, and the first posterior portion 82 of the lower vertebral body V, and a second of the spinal implants 10' is positioned on the anterior portion 80, the second lateral portion 88, and the second posterior portion 84 of the lower vertebral body V. More specifically, a portion of the extended end portion 14' of the first one of the spinal implants 10' rests on the anterior portion 80, a portion of the first one of the spinal implants 10' at the connection between the body portion 12' and the extended end portion 14' rests on the first lateral portion 86, and a portion of the body portion 12' of the first one of the spinal implants 10' adjacent the proximal end surface 30' rests on the first posterior portion 82; and a portion of the extended end portion 14' of the second one of the spinal implants 10' rests on the anterior portion 80, a portion of the second one of the spinal implants 10' at the connection between the body portion 12' and the extended end portion 14' rests on the second lateral portion 88, and a portion of the body portion 12' of the second one of the spinal implants 10' adjacent the proximal end surface 30' rests on the second posterior portion 84.

Although not shown, the spinal implant 10' would also contact similar locations of a cortical rim of the upper vertebral body across the disc space from the lower vertebral body V. Given the placement of the spinal implant 10', the arcuate shapes of the upper surface 32' and the lower surface 34' facilitate the distribution of the load to the strongest part of the vertebral bodies at the cortical rim C.

The insertion tool 100 also can be used to facilitate positioning the spinal implant 10' in the disc space. Furthermore, the spinal implant 10', as depicted in FIG. 6, can be inserted into the disc space from substantially lateral or substantially posterior directions as part of a TLIF procedure or a PLIF procedure, respectively. The spinal implant 10' could also be inserted from additional different insertion directions, and with different positions for the tool-engaging aperture 42', the first tool-engaging recess 44', the second tool-engaging recess 46', or other engagement features, the spinal implant 10' could be inserted in different orientations relative to the insertion tool 100. For example, the tool-engaging aperture 42', the first tool-engaging recess 44', the second tool-engaging recess 46', or other engagement features could be provided on the extended end portion 14', and the insertion tool 100 could be used to insert the spinal implant 10' at an insertion orientation afforded by the different placement of these engagement features.

The insertion tool 100, as depicted in FIGS. 5 and 6, includes an outer shaft portion 102, an inner shaft portion 104, a head portion 106, a mid-longitudinal axis $L_3$, an interior cavity (not shown), and a handle portion (not shown). The interior cavity extends through the outer shaft portion 102 and a portion of the head portion 106, and the inner shaft portion 104 is received within the interior cavity. Furthermore, the handle portion is attached to the inner shaft portion 104, the inner shaft portion 104 is rotatable with the interior cavity, and portions of the inner shaft portion 104 are moveable out of and into the interior cavity via actuation of the handle portion. As discussed below, the inner shaft portion 104 includes an end portion 108 that can include threads (not shown) for engaging the threads of the tool-engaging aperture 42, and can be extended and retracted relative to the head portion 106 to engage the spinal implants 10 and 10'.

The head portion 106, as depicted in FIG. 5, includes a first ear portion 110, a second ear portion 112, a first prong 114, a second prong (not shown), a recess 118, a first concave end surface 120, and a second concave end surface 122. The first prong 114 is provided on the distal end of the first ear portion 110 and is configured to engage the first tool-engaging recess 44; the second prong is provided on the distal end of the second ear portion 112 and is configured to engage the second tool-engaging recess 46; the recess 118 is positioned between the first ear portion 110 and the second ear portion 112; and the first concave end surface 120 and the second concave end surface 122 are configured to contact at least portions of the proximal end surfaces 30 and 30'.

To engage the spinal implants 10 and 10', the first prong 114 is received in the first tool-engaging recess 44, the second prong is received in the second tool-engaging recess 46, and a portion of the inner shaft portion 104 is extended through the recess 118 and the end portion 108 threaded into the tool-engaging aperture 42 via manipulation of the handle portion. After such engagement, the spinal implants 10 and 10' can be manipulated into positions within the disc space via the above-discussed procedures. When the spinal implants 10 and 10' are attached to the insertion instrument 100, the mid-longitudinal $L_1$ and the mid-longitudinal axis $L_3$ are oriented in alignment with one another, and thus, insertion directions thereof can also be aligned with the mid-longitudinal axes $L_1$ and $L_3$. The spinal implants 10 and 10' can be separated from the insertion tool 100 by reversing the order of the engagement. After separation, the insertion tool 100 can then be removed from the body of the patient.

Figure 7:
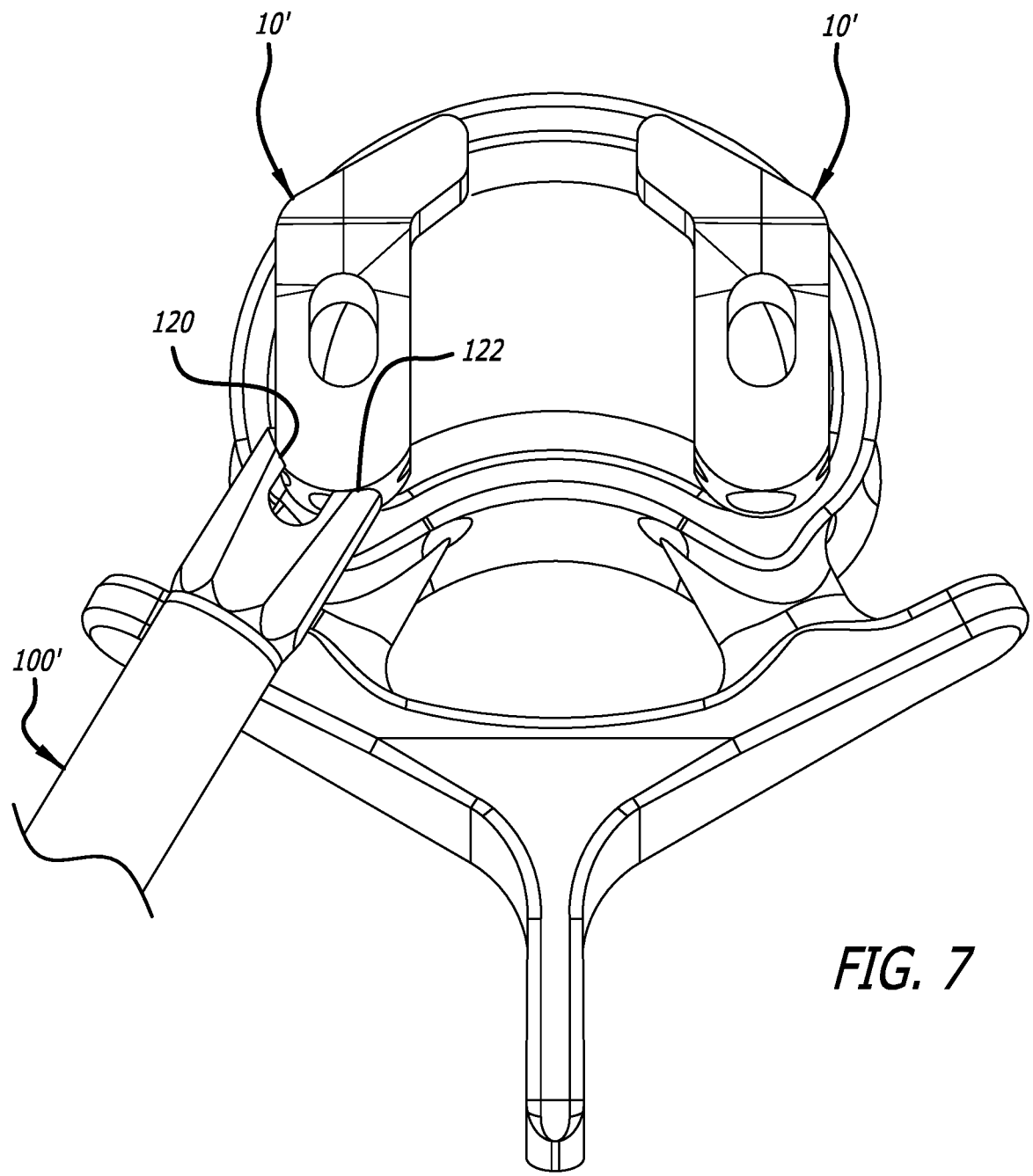
FIG. 7 is a top, rear, perspective view that illustrates insertion of the spinal implants of FIG. 4 into position relative to a lower one of adjacent vertebral bodies in a disc space using a second embodiment of an insertion instrument of the present disclosure.

As depicted in FIG. 7, an insertion instrument 100' is provided that optionally does not include the first prong 114 and the second prong 116. Like the insertion instrument 100, the insertion instrument 100' includes the first concave end surface 120 and the second concave end surface 122. The spinal implants 10 and 10' can be configured to include one or more tool-engagement apertures (not shown) facilitating engagement with corresponding engagement features provided on the inner shaft portion 104. The one or more tool-engagement apertures can be in different locations than the tool-engaging aperture 40, and these different locations afford insertion directions of the implants 10 and 10' in orientations with the longitudinal axis $L_1$ of the body portions 12 and 12' being transverse to the longitudinal axis $L_3$ of the insertion instrument 100'. In addition or alternatively to the above-discussed tool-engagement apertures, other engagement features can be configured to facilitate engagement by an insertion tool at a first engagement angle to the spinal implants 10 and 10', facilitate insertion of the spinal implants 10 and 10' at a first insertion angle using the insertion tool, facilitate release of the spinal implants 10 and 10' by the insertion tool, facilitate reengagement by the insertion tool at a different second engagement angle to the spinal implants 10 and 10', and then facilitate continued insertion of the spinal implants 10 and 10' at a different second insertion angle using the insertion tool. This process could be continued or repeated as necessary using additional different engagement angles and insertion angle. And this process could be used to rotate or spin the spinal implants 10 and 10' around anatomical features or into position within the disc space.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

I claim:

1. A unitary interbody spinal implant for implantation into a disc space between an upper vertebral body and a lower vertebral body, the implant comprising:
   a body portion having a proximal first end, an opposite distal second end, a proximal end surface at and adjacent the proximal first end, an upper surface, a lower surface, a first lateral side surface, a second lateral side surface, and a first mid-longitudinal axis extending through the proximal first end and the distal second end of the body portion,
   the upper surface and the lower surface each being at least in part arcuate in a first plane perpendicular to the first mid-longitudinal axis,
   the upper surface and the lower surface each being at least in part arcuate in a second plane extending along the first mid-longitudinal axis and perpendicular to the first plane,
   the proximal end surface being at least in part arcuate in a third plane at and adjacent an intersection of the first mid-longitudinal axis with the proximal end surface, the third plane extending along the first mid-longitudinal axis and being perpendicular to the first plane,
   the proximal end surface extending between the first lateral side surface and the second lateral side surface, and
   the first lateral side surface and the second lateral side of the body portion terminating adjacent a fourth plane perpendicular to the first mid-longitudinal axis of the body portion; and
   an extended end portion having a proximal first end, an opposite distal second end, a distal end surface, an upper surface, a lower surface, a first lateral side surface, a second lateral side surface, and a second mid-longitudinal axis extending through the proximal first end and the distal second end of the extended end portion, the proximal first end of the extended end portion being located adjacent the distal second end of the body portion, the first lateral side surface and the second lateral side surface each including planar portions extending toward the distal end surface at a different acute angle relative to the fourth plane, and the second mid-longitudinal axis being transverse to the first mid-longitudinal axis,
   wherein the upper surface and the lower surface being arcuate in the first plane and the second plane provides for biconvex configurations adapted to contact endplates of the upper vertebral body and the lower vertebral body, respectively.

2. The interbody spinal implant of claim 1, wherein the proximal end surface approximates a portion of a circle in the third plane.

3. The interbody spinal implant of claim 2, wherein a first tool-engaging recess is formed in portions of the proximate end surface and the first lateral side surface of the body portion, and a second tool-engaging recess is formed in portions of the proximate end surface and the second lateral side surface of the body portion.

4. The interbody spinal implant of claim 1, wherein the upper surface and the lower surface of the body portion extend between the proximal first end and the distal second end.

5. The interbody spinal implant of claim 1, further comprising an aperture extending through the body portion between the upper surface and the lower surface.

6. The interbody spinal implant of claim 1, further comprising a first arcuate transition between the distal end surface and the first lateral side surface of the extended end portion, and a second arcuate transition between the distal end surface and the second lateral side surface.

7. The interbody spinal implant of claim 1, wherein the extended end portion includes a reverse taper from the proximal first end to the distal second end thereof.

8. The interbody spinal implant of claim 7, wherein the extended end portion includes a first height adjacent the proximal first end thereof and a second height adjacent the distal second end thereof, the first height being shorter than the second height.

9. The interbody spinal implant of claim 1, wherein a fifth plane extends along the second lateral side surface of the body portion, and portions of the extended end portion are disposed on each side of the fifth plane.

10. A unitary interbody spinal implant comprising:
    a body portion having a proximal first end, an opposite distal second end, a proximal end surface at and adjacent the proximal first end, an upper surface, a lower surface, a first lateral side surface, a second lateral side surface, and a first mid-longitudinal axis extending through the proximal first end and the distal second end of the body portion,
    the upper surface and the lower surface each being at least in part arcuate in a first plane perpendicular to the first mid-longitudinal axis,
    the upper surface and the lower surface each being at least in part arcuate in a second plane extending along the first mid-longitudinal axis and perpendicular to the first plane, and
    the proximal end surface being at least in part arcuate in a third plane at and adjacent an intersection of the first mid-longitudinal axis with the proximal end surface, the third lane extending along the first mid-longitudinal axis and being perpendicular to the first plane,
    the proximal end surface extending between the first lateral side surface and the second lateral side surface, and
    the first lateral side surface and the second lateral side of the body portion terminating adjacent a fourth plane perpendicular to first the mid-longitudinal axis of the body portion; and
    an extended end portion having a proximal first end, an opposite distal second end, a distal end surface, an upper surface, a lower surface, a first lateral side surface, a second lateral side surface, and a second mid-longitudinal axis extending through the proximal first end and the distal second end of the extended end portion, the proximal first end of the extended end portion being located adjacent the distal second end of the body portion, the first lateral side surface and the second lateral side surface each including planar portions extending toward the distal end surface at a different acute angle relative to the fourth plane, the second mid-longitudinal axis being transverse to the first mid-longitudinal axis, and portions of the extended end portion being located on each side of a fifth plane extending along the second lateral side surface.

11. The interbody spinal implant of claim 10, wherein the proximal end surface approximates a portion of a circle in the third plane.

12. The interbody spinal implant of claim 11, wherein a first tool-engaging recess is formed in portions of the proximate end surface and the first lateral side surface of the body portion, and a second tool-engaging recess is formed in portions of the proximate end surface and the second lateral side surface of the body portion.

13. The interbody spinal implant of claim 10, further comprising a first arcuate transition between the distal end surface and the first lateral side surface of the extended end portion, and a second arcuate transition between the distal end surface and the second lateral side surface.

14. The interbody spinal implant of claim 10, wherein the extended end portion includes a reverse taper from the proximal first end to the distal second end thereof.

15. The interbody spinal implant of claim 14, wherein the extended end portion includes a first height adjacent the proximal first end thereof and a second height adjacent the distal second end thereof, the first height being shorter than the second height.

16. A unitary interbody spinal implant comprising:
a body portion having a proximal first end, an opposite distal second end, a proximal end surface at and adjacent the proximal first end, an upper surface, a lower surface, and a first mid-longitudinal axis extending through the proximal first end and the distal second end of the body portion,
the upper surface and the lower surface each being at least in part arcuate in a first plane perpendicular to the first mid-longitudinal axis, and
the proximal end surface being at least in part arcuate in a second plane at and adjacent an intersection of the first mid-longitudinal axis with the proximal end surface, the second plane extending along the first mid-longitudinal axis and perpendicular to the first plane; and
an extended end portion having a proximal first end, an opposite distal second end, a distal end surface, an upper surface, a lower surface, and a second mid-longitudinal axis extending through the proximal first end and the distal second end of the extended end portion, the proximal first end of the extended end portion being located adjacent the distal second end of the body portion, a first lateral side surface and a second lateral side surface each including planar portions extending toward the distal end surface at a different acute angle relative to a third plane perpendicular to the first mid-longitudinal axis, the second mid-longitudinal axis being transverse to the first mid-longitudinal axis, and portions of the extended end portion being located on each side of a fourth plane extending along the second lateral side surface.

17. The interbody spinal implant of claim 16, wherein the proximal end surface approximates a portion of a circle in the second plane.

18. The interbody spinal implant of claim 17, wherein a first tool-engaging recess is formed in portions of the proximate end surface and a first lateral side surface of the body portion, and a second tool-engaging recess is formed in portions of the proximate end surface and a second lateral side surface of the body portion.

19. The interbody spinal implant of claim 16, wherein the extended end portion includes a reverse taper from the proximal first end to the distal second end thereof.

20. The interbody spinal implant of claim 19, wherein the extended end portion includes a first height adjacent the proximal first end thereof and a second height adjacent the distal second end thereof, the first height being shorter than the second height.

* * * * *